(12) United States Patent
Pratt

(10) Patent No.: US 6,733,541 B2
(45) Date of Patent: May 11, 2004

(54) COMPOSITION FOR THE DYEING OF HUMAN HAIR

(75) Inventor: Dominic Pratt, Darmstadt (DE)

(73) Assignee: KAO Corporation, Tokyo (JP)

( * ) Notice: Subject to any disclaimer, the term of this patent is extended or adjusted under 35 U.S.C. 154(b) by 89 days.

(21) Appl. No.: 10/095,917

(22) Filed: Mar. 13, 2002

(65) Prior Publication Data

US 2003/0019052 A1 Jan. 30, 2003

(30) Foreign Application Priority Data

Mar. 15, 2001 (DE) .......................... 101 12 437

(51) Int. Cl.$^7$ ................................. A61K 7/13
(52) U.S. Cl. .................. 8/405; 8/406; 8/407; 8/421; 8/614
(58) Field of Search ............... 8/405, 406, 407, 8/421, 614

(56) References Cited

FOREIGN PATENT DOCUMENTS

| DE | 1 922 400 | 12/1969 |
|---|---|---|
| DE | 201 04 442 | 8/2002 |
| EP | 0 079 540 | 5/1983 |
| JP | 7-21492 | 8/1995 |
| JP | 7-304273 | 11/1995 |
| JP | 11-349874 | 12/1999 |

OTHER PUBLICATIONS

Chemical Abstract, Columbus, Ohio, US vol. 121, 8, Sep. 22, 1994.*

\* cited by examiner

Primary Examiner—Yogendra M. Gupta
Assistant Examiner—Eisa Elhilo
(74) Attorney, Agent, or Firm—Oblon, Spivak, McClelland, Maier & Neustadt, P.C.

(57) ABSTRACT

The invention concerns a composition for the dyeing of human hair on the basis of at least one direct-acting hair dyestuff, characterized in that it comprises at least one dyestuff of the formula (1)

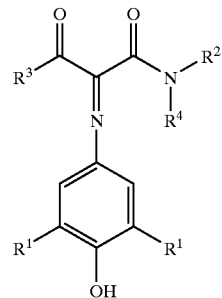

(1)

wherein $R^1$ is a halogen atom; $R^2$ and $R^4$ are an optionally OH— or $NH_2$-substituted $C_1$–$C_4$-alkyl group or phenyl group and $R^3$ stands for H, or an optionally OH— or $NH_2$-substituted $C_1$–$C_4$-alkyl group or phenyl group.

12 Claims, No Drawings

COMPOSITION FOR THE DYEING OF HUMAN HAIR

The invention concerns a composition for the dyeing of human hair on aqueous basis, which comprises at least one direct-acting hair dyestuff. Such hair dyeing compositions have been known for some time.

They usually comprise several anionic or cationic direct-acting dyestuffs and, in difference to the permanent hair dyeing compositions on the basis of oxidation dyestuff precursor products, they require no prior development with oxidation agents.

These direct-acting compositions are either applied together with surface-active substances as so-called tinting shampoos, or they are applied onto the hair as lotions, emulsions or thickened lotions, i.e. gels.

With regard to their color stability and especially intensity as well as evenness of the coloration and color gloss, these direct-acting hair dyeing compositions can still be improved.

The invention therefore starts from the task of creating a hair dyeing composition on the basis of direct-acting dyestuffs, which can be applied onto the hair as a lotion, emulsion, solution, gel, suspension or, also, with the addition of propellants, as aerosol preparation, and which shows excellent coloration properties, providing stable colorations over an extended period of time.

This problem is solved by adding to such a composition at least one direct-acting dyestuff on the basis of a compound of formula (1)

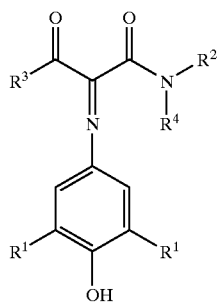

(1)

wherein $R^1$ is a halogen atom; $R^2$ and $R^4$ are an optionally OH— or $NH_2$-substituted $C_1$–$C_4$-alkyl group or phenyl group and $R^3$ stands for $H_1$ or an optionally OH— or $NH_2$-substituted $C_1$–$C_4$-alkyl group or phenyl group.

Preferred compounds are those of the formulas (2) and (3)

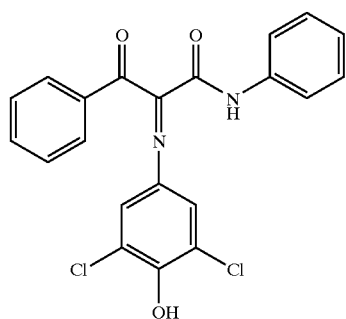

(2)

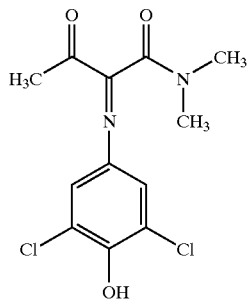

(3)

The preparation of these compounds is known per se and is carried out by transfer of the respectively substituted acetamides or acetanilides with the respectively substituted haloaminobenzoles.

The colors thus obtained are mainly in the range of intensive yellow and gold but can be varied by the addition of further dyestuff shades.

The proportion of direct-acting dyestuffs in the compositions according to the invention is variable and ranges between about 0.001% to about 5%, preferably 0.01% to 2.5%, in particular 0.1% to 1% by weight, calculated to the total composition.

As stated above, in addition to the compounds of formula (1), it is possible to incorporate further direct-acting hair dyestuffs to modify the shades.

Preferred are the so-called "Arianor" dyestuffs; see K. Schrader, "Grundlagen und Rezepturen der Kosmetika", 2nd Ed., (1989), p. 811.

Especially suited basic (cationic) dyestuffs are.

| | |
|---|---|
| Basic Blue 6, | C.I.-No. 51,175; |
| Basic Blue 7, | C.I.-No. 42,595; |
| Basic Blue 9, | C.I.-No. 52,015; |
| Basic Blue 26, | C.I.-No. 44,045; |
| Basic Blue 41, | C.I.-No. 11,154; |
| Basic Blue 99, | C.I.-No. 56,059; |
| Basic Brown 4, | C.I.-No. 21,010; |
| Basic Brown 16, | C.I.-No. 12,250; |
| Basic Brown 17, | C.I.-No. 12,251; |
| Natural Brown 7, | C.I.-No. 75,500; |
| Basic Green 1, | C.I.-No 42,040; |
| Basic Red 2, | C.I.-No. 50,240; |
| Basic Red 12 | C.I.-No. 48,070; |
| Basic Red 22, | C.I.-No. 11,055; |
| Basic Red 76, | C.I.-No. 12,245; |
| Basic Violet 1, | C.I.-No. 42,535; |
| Basic Violet 3, | C.I.-No. 42,555; |
| Basic Violet 10, | C.I.-No. 45,170; |
| Basic Violet 14, | C.I.-No. 42,510; |
| Basic Yellow 57, | C.I.-No. 12,719. | as well as the dyestuffs known from EP 0681 464 B1.

It is, of course, also possible to use the respective direct-acting plant dyestuffs or also anionic (acidic), direct-acting hair dyestuffs.

These are customarily also used in an amount of about 0.005% to about 5%, preferably about 0.05% to about 2.5%, in particular about 0.1% to about 1% by weight, calculated to the total composition, which is present as solution, dispersion, emulsion, gel or aerosol preparation for direct application.

Suitable as anionic dyestuffs are, for example:

| | |
|---|---|
| Acid Black 1, | C.I.-No. 20,470; |
| Acid Blue 1, | C.I.-No. 42,045; |
| Food Blue 5, | C.I.-No. 42,051; |
| Acid Blue 9, | C.I.-No. 42,090; |
| Acid Blue 74, | C.I.-No. 73,015; |
| Acid Red 18, | C.I.-No. 16,255; |
| Acid Red 27, | C.I.-No. 16,185; |
| Acid Red 87, | C.I.-No. 45,380; |
| Acid Red 92, | C.I.-No. 45,410; |
| Acid Orange 7, | C.I.-No. 15,510; |
| Acid Violet 43, | C.I.-No. 60,730; |
| Acid Yellow 1, | C.I.-No. 10,316; |
| Acid Yellow 23, | C.I.-No. 19,140; |
| Acid Yellow 3, | C.I.-No. 47,005; |
| Food Yellow No. 8, | C.I.-No 14,270; |
| D&C Brown No. 1, | C.I.-No. 20,170; |
| D&C Green No. 5, | C.I.-No. 61,570; |
| D&C Orange No. 4, | C.I.-No. 15,510; |
| D&C Orange No. 10, | C.I.-No. 45,425:1; |
| D&C Orange No. 11, | C.I.-No. 45,425; |
| D&C Red No. 21, | C.I.-No. 45,380:2; |
| D&C Red No. 27, | C.I.-No. 45,410:1; |
| D&C Red No. 33, | C.I.-No. 17,200; |
| D&C Yellow No. 7, | C.I.-No. 45,350:1; |
| D&C Yellow No. 8, | C.I.-No. 45,350; |
| FD&C Red No. 4, | C.I.-No. 14,700; |
| FD&C Yellow No. 6, | C.I.-No 15,985. |

Also possible is the use of plant dyestuffs alone or in combination with synthetic direct-acting dyestuffs, for example henna (red or black), alkanna root, laccaic acid, indigo, logwood powder, madder root and rhubarb powder, etc.

The compositions according to the invention may also comprise at least one oxidation dyestuff precursor product, i.e. a developing and/or coupling substance.

Examples of developing substances are in particular 1,4-diaminobenzene, 2,5-diaminotoluene, tetraaminopyrimidines, triaminohydroxypyrimidines, 1,2,4-triaminobenzene, 2-(2,5-diaminophenyl)ethanol, 2-(2-hydroxyethylamino)-5-aminotoluene and 1-amino-4-bis-(2'-hydroxyethyl)aminobenzene or the water-soluble salts thereof; examples for coupling substances are resorcinol, 2-methylresorcinol, 4-chlororesorcinol, 2-amino-4-chlorophenol, 4-(N-methyl)aminophenol, 2-aminophenol, 3-aminophenol, 1-methyl-2-hydroxy-4-aminobenzene, 3-N,N-dimethylaminophenol, 4-amino-3-methylphenol, 5-amino-2-methylphenol, 6-amino-3-methylphenol, 3-amino-2-methylamino-6-methoxypyridine, 2-amino-3-hydroxypyridine, 4-aminodiphenylamine, 4,4'-diaminodiphenylamine, 2-dimethylamino-5-aminopyridine, 2.6-diaminopyridine, 1,3-diaminobenzene, 1-amino-3-(2'-hydroxyethylamino)benzene, 1-amino-3-[bis(2'-hydroxyethyl)amino]benzene, α-naphthol, 1,4-diamino-2-chlorobenzene, 4,6-dichlororesorcinol, 1,3-diaminotoluene, 1-hydroxynaphthalene, 4-hydroxy-1,2-methylendioxybenzene, 1,5-dihydroxynaphthalene, 1,7-dihydroxynaphthalene, 2,7-dihydroxynaphthalene, 2,4-diamino-3-chlorophenol and/or 1-methoxy-2-amino-4-(2'-hydroxyethylamino)benzene, whereby this list is not complete.

Developing and coupling substances are preferably present in a molecular ratio of 1:3 to 5:1, in particular about 1:1 and about 3:1; their proportion in the dyestuff compositions used according to the invention can each be about 0.05% to about 5% by weight, depending on the desired coloration.

Used as oxidizing agents in such oxidation dyestuff precursor products are mainly diluted hydrogen peroxide solutions, emulsions or gels, possible but less common is also the use of further peroxides such as earth alkali peroxides, urea peroxide, melamine peroxide, etc., in the respective stoic amounts.

The oxidation dyestuff compositions can be used as solutions, creams, pastes, gels, aerosols, etc.

The hair dyeing composition according to the invention may also comprise surface-active substances, in the event the composition is a tinting shampoo, these are obligatory in any case.

Such surface-active substances can be anionic, nonionic, cationic or amphoteric or zwitterionic surfactants.

Preferred for non-tinting shampoos are nonionic, amphoteric or zwitterionic and cationic surfactants in an amount between about 0.5% and about 5% by weight, calculated to the total composition.

Suited nonionic surfactants are compounds from the category of alkyl polyglucosides with the general formula (4)

$$R^5-O-(CH_2CH_2O)_p-Z_q \qquad (4)$$

wherein $R^5$ is an alkyl group with 8 to 20, preferably 10 to 14 carbon atoms Z is a saccharide group with 5 to 6 carbon atoms, p is a number from 0 to 10, and q is a number between 1 and 5, preferably 1.1 to 2.5.

Further nonionic surfactants useful in the compositions according to invention are $C_{10}$–$C_{22}$-fatty alcohol ethoxylates.

Especially suited $C_{10}$–$C_{22}$-fatty alcohol ethers are the alkyl polyglycol ethers known by the generic terms "Laureth", "Myristeth", "Oleth", "Ceteth", "Deceth", "Steareth" and "Ceteareth" according to the CTFA nomenclature, including addition of the number of ethyleneoxide molecules, e.g., "Laureth-16".

The average degree of ethoxylation thereby ranges between about 2.5 and about 25, preferably about 10 and about 20.

Other additionally useful nonionic surfactants are, for example, the various sorbitan esters, such as polyethylene glycol sorbitan stearic acid ester, fatty acid polyglycol ester or also mixed condensates of ethyleneoxide and propyleneoxide, as they are on the market, for example, under the trade name "Pluronics™".

Further additionally useful surfactants are amineoxides. Such amineoxides are state of the art, for example $C_{12}$–$C_{18}$-alkyl dimethyl aminoxides such as lauryl dimethyl aminoxide, $C_{12}$–$C_{18}$-alkyl amidopropyl or ethyl aminoxides, $C_{12}$–$C_{18}$-alkyl di(hydroxyethyl) or (hydroxypropyl) aminoxides, or also aminoxides with ethyleneoxide and/or propyleneoxide groups in the alkyl chain.

Suitable amineoxides are on the market, for example, under the trade names "Ammonyx®", "Aromox®" or "Genaminox®".

Further optional surfactant components are fatty acid mono- and dialkanolamides, such as coco fatty acid monoethanolamide and myristic fatty acid monoisopropanolamide.

Suitable amphoteric or zwitterionic surfactants are in particular the various known betaines such as fatty acid amidoalkyl betaines and sulfobetaines; for example lauryl hydroxy sulfobetaine: long-chain alkyl amino acids, such as cocoaminoacetate, cocoaminopropionate and sodium cocoamphopropionate and acetate have also proven suitable.

In detail it is possible to use betaines or sulfobetaines with the general formulas (5) to (8)

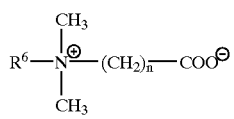

(5)

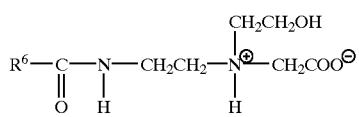

(6)

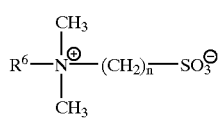

(7)

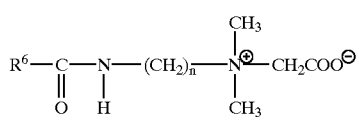

(8)

wherein $R^6$ is a $C_6$–$C_{18}$-alkyl group and n is 1 to 3.

Preferred are fatty acid amidoalkyl betaines, in particular cocoamidopropyl betaine, and cocoamphoacetate and propionate, in particular the sodium salts thereof.

Especially preferred are mixtures of cocoamidopropyl betaine and cocoampho-acetate, in particular in a weight proportion of 3:1 to 1:3, especially 2:1 to 1:1.

Suitable cationic surfactants are, for example, long-chain quaternary ammonium compounds which can be used alone or in admixture with one another, such as cetyl trimethyl ammonium chloride, dimethyl diethyl ammonium chloride, trimethyl cetyl ammonium bromide, stearyl trimethyl ammonium chloride, dimethyl stearyl benzyl ammonium chloride, benzyl tetradecyl dimethyl ammonium chloride, dimethyl dihydrogenated tallow ammonium chloride, lauryl pyridinium chloride, lauryl dimethyl benzyl ammonium chloride, behenyl trimethyl ammonium chloride, lauryl trimethyl ammonium chloride, tris-(oligooxyethyl) alkyl ammonium phosphate, cetyl pyridinium chloride, etc. Useful are also the quaternary ammonium salts disclosed in EP-A472 107.

Further suited long-chain ammonium compounds are esterquats of the general formula (9)

The anion $Y^-$ is preferably a halide, such as $Cl^-$ or $Br^-$, a lower alkyl sulfate, for example, methosulfate and ethosulfate, or an alkyl phosphate, however, it is of course also possible to use other groups.

These compounds are known and are on the market, for example, under the trade names "Schercoquat®", "Dehyquart® F30" and "Tetranyl®". Use of these "esterquats" in hair conditioning compositions is also known and disclosed, for example, in WO-A 93/10748, WO-A 92/06899 and in WO-A 94/16677.

Also suited are amidoquats of the general formula (10)

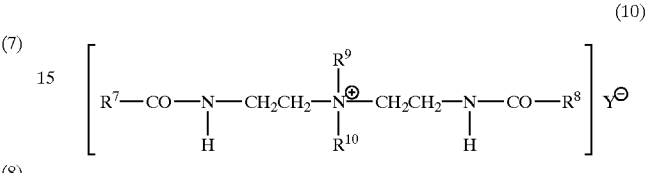

(10)

wherein $R^7$, $R^8$, $R^9$, $R^{10}$ and $Y^-$ have the above meanings.

It is self-understood that mixtures of the various surfactants are also possible to the extent these are compatible with each other.

A further desirable component in the hair dyeing compositions according to the invention is a $C_3$–$C_6$-alkanediol or the ethers thereof, in particular a mono-$C_1$–$C_3$-alkyl ether.

Preferred substances in this context are 1,2- and 1,3-propanediol, 1-methoxy-propanol(-2), 1-ethoxypropanol(-2), 1,3- and 1,4-butanediol, diethylene glycol and the monomethyl and monoethyl ethers thereof.

The proportion of these diols preferably ranges between 0.5% and 30%, preferably about 1% to about 15%, in particular about 5% to about 10% by weight, calculated to the total hair dyeing composition.

Also useful in addition to the $C_3$–$C_6$-alkanediols or the ethers thereof are monoalcohols, such as ethanol, propanol-1, propanol-2, as well as polyalcohols such as glycerol and hexanetriol, ethyl carbitol, benzyl alcohol, benzyloxy ethanol as well as propylene carbonate (4-methyl-1,3-dioxolane-2-one), N-alkyl pyrrolidone and urea.

Further possible components are cationic, anionic, nonionic and amphoteric polymers, preferably in an amount from about 0.1% to about 5%, in particular about 0.25% to 2.5% by weight, calculated to the total hair dyeing composition.

These compositions can also contain further conditioning agents such as fats and oils. These are, for example, sun-

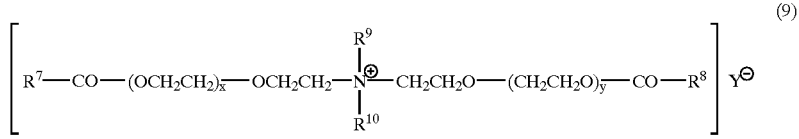

(9)

wherein $R^7$ and $R^8$ stand for an optionally hydroxy-substituted $C_8$–$C_{22}$-alkyl or alkenyl group, $R^9$ and $R^{10}$ stand for a $C_1$–$C_3$-alkyl group or a group —$CH_2$—$CH_2$—O—($CH_2CH_2O$)$_z$H, x, y and z stand for 0 to 5 and Y stands for an anion.

A compound of formula (9) especially preferred within the scope of the invention is one wherein the groups $R^7$ and $R^8$ each stand for an oleyl group or a $C_{12}$–$C_{18}$-alkyl group, the group $R^9$ is a methyl group and the group $R^{10}$ is a group. $CH_2$—$CH_2$—O—($CH_2CH_2O$)$_z$H.

flower oil, almond oil, peach kernel oil, wheat germ oil, macadamia nut oil, night primrose oils jojoba oil, castor oil, or also olive or soya oil, lanolin and the derivatives thereof, as well as mineral oils such as paraffin oil and petrolatum. Synthetic oils and waxes are, for example, silicone oils, polyethylene glycols, etc.

Further suitable hydrophobic components are in particular fatty acid esters such as isopropyl myristate, palmitate, stearate and isostearate, oleyl oleate, isocetyl stearate, hexyl laurate, dibutyl adipate, dioctyl adipate, myristyl myristate, oleyl erucate, polyethylene glycol and polyglyceryl fatty acid esters such as PEG-7-glyceryl cocoate, cetyl palmitate, etc.

In the event that the compositions according to the invention are emulsions, they naturally contain the customary emulsifiers.

The compositions according to the invention can also contain long-chain fatty acids. Preferred fatty acids are those with 10 to 24, in particular 12 to 22 carbon atoms, in an amount from about 0.5% to 15% by weight, in particular 1% to 10% by weight, calculated to the total composition Especially suited are behenic acid and stearic acid; however, it is also possible to incorporate other fatty acids, such as, for example, myristic acid, palmitic acid or oleic acid, or also mixtures of natural or synthetic fatty acids, such as coco fatty acid.

The viscosity of the compositions according to the invention preferably ranges from about 1000 to about 60,000, in particular about 5,000 to 50,000, especially from about 10,000 to 40,000 mPa.s at 20° C., measured in a Brookfield rotation viscosimeter with a no. 5 spindle at 5 rpm.

The pH-value is preferably in the acidic range between about 2 and 7, for example between 2.5 and 6, in particular about 3 and 5.5.

In the event the compositions are a tinting shampoo, in addition to the surface-active substances named above, these can naturally also contain anionic surfactants.

Suitable anionic surfactants are present in an amount from at least 5% to about 50% by weight, preferably 10% to 25% by weight, calculated to the total composition.

These are anionic surfactants of the sulfate, sulfonate, carboxylate and alkyl phosphate type, especially, of course, those customarily used in shampoo compositions, for example, the known $C_{10}$–$C_{18}$-alkyl sulfates, and in particular the respective ether sulfates, for example, $C_{12}$–$C_{14}$-alkyl ether sulfate, lauryl ether sulfate, especially with 1 to 4 ethylene oxide groups in the molecule, furthermore monoglyceride (ether) sulfates, fatty acid amide sulfates, obtained by ethoxylation and subsequent sulfatation of fatty acid alkanolamides, and the alkali salts thereof, as well as the salts of long-chain mono- and dialkyl phosphates, which constitute mild, skin-compatible detergents.

Further useful anionic surfactants are α-olefin sulfonates or the salts thereof, and in particular alkali salts of sulfosuccinic acid semiesters, for example the disodium salt of monooctyl sulfosuccinate, and alkali salts of long-chain monoalkyl ethoxysulfosuccinates.

Suitable surfactants of the carboxylate type are alkyl polyether carboxylic acids and the salts thereof of the formula (11)

$$R^{11}\text{—}(CH_2CH_2O)_a\text{—}CH_2\text{—}COOX \quad (11)$$

wherein $R^{11}$ is a $C_8$–$C_{20}$-alkyl group, preferably a $C_{12}$–$C_{14}$-alkyl group, a is a number from 1 to 20, preferably 2 to 17, and X is H or preferably a cation of the group sodium, potassium, magnesium and ammonium, which may optionally be hydroxyalkyl-substituted, as well as alkyl amido polyether carboxylic acids of the general formula (12)

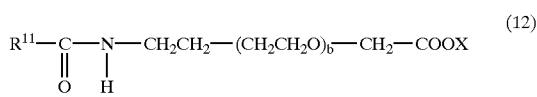

$$R^{11}\text{—}\underset{\underset{O}{\|}}{C}\text{—}\underset{\underset{H}{|}}{N}\text{—}CH_2CH_2\text{—}(CH_2CH_2O)_b\text{—}CH_2\text{—}COOX \quad (12)$$

wherein $R^{11}$ and X have the above meanings and b is in particular a number from 1 to 10, preferably 2.6 to 5.

Such products are known and on the market, for example under the trade names "AKYPO®" and "AKYPO-SOFT®".

$C_8$–$C_{20}$-acylisethionates can also be used alone or in admixture with other surfactants, as well as sulfofatty acids and the esters thereof.

It is also possible to use mixtures of several anionic surfactants, for example a mixture of an α-olefin sulfonate and a sulfosuccinate, preferably in a proportion of 1:3 to 3:1, or an ether sulfate and a polyether carboxylic acid or alkyl amidoether carboxylic acid.

An overview of the anionic surfactants used in liquid body cleansing compositions can be found in the monography of K. Schrader, "Grundlagen und Rezepturen der Kosmetika", 2nd Ed., (1989, Hüthig Buchverlag), pp. 683 to 691. The preferred amount of anionic surfactants in the tinting shampoos according to the invention ranges between about 5% and 30% by weight, in particular from about 7.5% to about 25% by weight, especially preferred from about 10% to about 20% by weight, calculated to the total composition, depending on whether it is a concentrate.

As a preferred embodiment, the tinting shampoos according to the invention preferably contain a mixture of one of the afore-mentioned anionic surfactants and at least one $C_8$–$C_{22}$-acyl aminocarboxylic acid or the water-soluble salts thereof, preferably in an amount from 0.5% to 10%, in particular 1% to 7.5% by weight, calculated to the total composition.

Especially preferred are N-lauroyl glutamate, in particular its sodium salt Further suitable N-acyl aminocarboxylic acids are, for example, N-lauroyl sarcosinate, N-$C_{12}$–$C_{18}$-acyl aspartic acid, N-myristoyl sarcosinate, N-oleoyl sarcosinate, N-lauroyl methyl alanine, N-lauroyl lysine and N-lauroyl aminopropyl glycine, preferably in form of the water-soluble alkali or ammonium, in particular sodium salts thereof.

The following Examples illustrate the invention.

EXAMPLE I 0.5 g of benzoyl acetanilide are dissolved in alkaline ethanol, added thereto are 0.5 g of 4-amino-2,6-dichlorophenol as well as 0.1 g of potassium persulfate. This mixture is stirred for one hour. Thereafter the precipitate is filtered, dried, subsequently dissolved in acetone, filtered, the acetone then steamed, whereby a yellow dyestuff of the formula (2) is obtained.

EXAMPLE II 0.5 g of N,N-dimethyl acetoacetamide were added to 100 ml of an alkaline, aqueous solution of 0.5 g of 4-amino-2,6-dichlorophenol and 0.1 g of 50% $H_2O_2$ and stirred for 12 hours. The precipitate was subsequently filtered, dried, dissolved in acetone, filtered, the filtrate was then steam-dried, whereby a yellow dyestuff of the formula (3) was obtained.

Examples of Embodiments

The hair dyestuffs according to the general formula (1) can be applied onto the hair in a manner known per se, where they achieve stable, long-lasting, brilliant coloration results resistant to light, shampooing, perspiration and the environment.

In the coloration tests described hereafter, 0.1 g of the dyestuff disclosed in Examples I or II was first dissolved in 0.5 g of ethanol, and this pre-solution was dissolved in a mixture of 0.5 g of benzyl alcohol and 9 g of water, adjusted to a pH-value of 10 with ammonia.

A strand of undamaged, white goat hair was immersed in this solution for 20 minutes at 30° C. After the coloration process the strand was washed with shampoo and subsequently dried.

A customary Minolta color-measuring device was used in a known manner to determine the initial value of the obtained colorations and their relation to each other, and the ΔE-value was calculated in a customary manner known as a measure for color intensity.

Result:

| Dyestuff | L | a | b | ΔE | Coloration |
|---|---|---|---|---|---|
| Undyed | 80 | 1 | 14 | — | White goat hair |
| Dyestuff according to Example I | 58 | 11 | 51 | 44.2 | Glossy, intensive yellow |
| Dyestuff according to Example II | 61 | 4 | 44 | 35.6 | Glossy, intensive golden-yellow |

These coloration tests show the surprising coloration properties of the direct-acting dyestuffs according to the invention.

The colorations achieved with the hair dyestuffs according to the invention are also remarkable with regard to their higher resistance against shampooing, environmental influences such as sun, perspiration, rain, etc., in comparison to hair colorations obtained with convention direct-acting hair dyestuffs.

What is claimed is:

1. A composition for the dyeing of human hair on the basis of at least one direct-acting dyestuff, which comprises:

at least one dyestuff of formula (1)

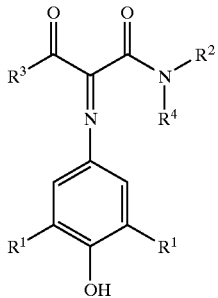

(1)

wherein $R^1$ is a halogen atom, $R^2$ and $R^4$ stand for an optionally substituted OH— or $NH_2$-substituted $C_1$–$C_4$-alkyl group or phenyl group and $R^3$ stands for H, or an optionally OH— or $NH_2$-substituted $C_1$–$C_4$-alkyl group or phenyl group.

2. A method of dyeing human hair, comprising:

applying a hair dye composition containing a dyestuff of formula (1)

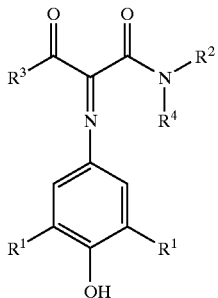

(1)

wherein $R^1$ is a halogen atom, $R_2$ and $R_4$ stand for an optionally substituted OH— or $NH_2$-substituted $C_1$–$C_4$- alkyl group or phenyl group and $R^3$ stands for H, or an optionally OH— or $NH_2$-substituted $C_1$–$C_4$-alkyl group or phenyl group, to the hair.

3. The composition according to claim 1, comprising 0.001% to 5% by weight, based on the total composition, of at least one dyestuff of formulas (2) and (3)

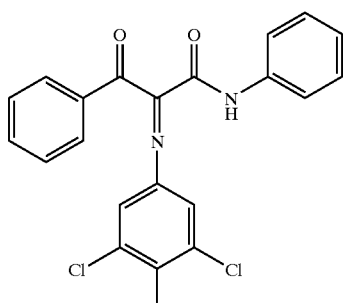

(2)

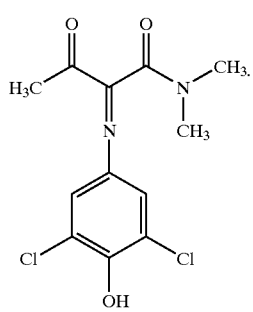

(3)

4. A method of dyeing human hair, comprising:

applying a hair dye composition containing a dyestuff of formulas (2) and/or (3)

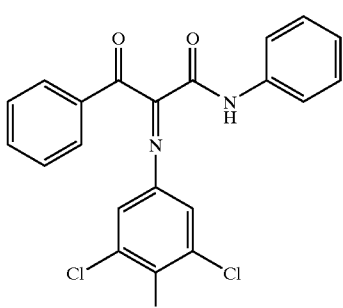

(2)

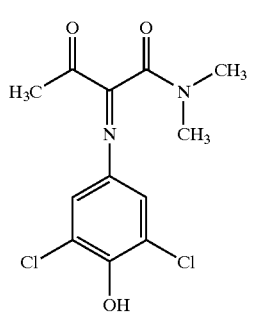

(3)

to human hair.

5. The composition according to claim 1 or 3, which comprises at least one oxidation dyestuff precursor.

6. The composition according to claim 1, wherein the content of the dyestuff of formula (1) ranges from 0.001 to about 5% by weight based on the weight of composition.

7. The composition according to claim 1, wherein the composition contains at least one surfactant selected from the group consisting of anionic surfactants, nonionic surfactants, cationic surfactants and amphoteric or zwitterionic surfactants.

8. The composition according to claim 7, wherein the content of the at least one surfactant ranges from 0.5 to about 5% by weight based on the weight of composition.

9. The composition according to claim 1, which contains a long-chain fatty acid in an amount of about 0.5% to 15% by weight, based on the weight of the composition.

10. The composition according to claim 1, which has a viscosity ranging from about 1000 to about 60,000 mPa·s at 20° C.

11. The composition according to claim 1, which has a pH ranging from 2 to 7.

12. The composition according to claim 1, wherein the oxidation dyestuff precursor is comprised of developer and coupler in a mole ratio ranging from 1:3 to 5:1.

* * * * *